United States Patent [19]
McPherson et al.

[11] Patent Number: 6,048,321
[45] Date of Patent: Apr. 11, 2000

[54] GUIDE ASSEMBLY FOR A BIOPSY DEVICE

[75] Inventors: William E. McPherson, 14605 Anchoret Rd., Tampa, Fla. 33624; J. Stephen TenBarge, Clearwater, Fla.

[73] Assignee: William E. McPherson, Tampa, Fla.

[21] Appl. No.: 09/165,054

[22] Filed: Oct. 2, 1998

Related U.S. Application Data

[60] Provisional application No. 60/061,882, Oct. 10, 1997.

[51] Int. Cl.$^7$ ...................................................... A61B 10/00
[52] U.S. Cl. .......................... 600/564; 600/567; 606/130; 606/170
[58] Field of Search .................................... 600/417, 429, 600/562, 564, 566, 567, 568; 606/130, 167, 170, 184, 185

[56] References Cited

U.S. PATENT DOCUMENTS

| | | | |
|---|---|---|---|
| 2,541,542 | 2/1951 | Perez et al. ................................... | 128/2 |
| 4,682,606 | 7/1987 | DeCaprio ................................... | 128/754 |
| 4,785,826 | 11/1988 | Ward ........................................ | 128/754 |
| 4,926,877 | 5/1990 | Bookwalter .............................. | 128/754 |
| 5,111,828 | 5/1992 | Kornberg et al. ........................ | 128/754 |
| 5,197,484 | 3/1993 | Kornberg et al. ........................ | 128/754 |
| 5,251,641 | 10/1993 | Xavier ...................................... | 128/754 |
| 5,353,804 | 10/1994 | Kornberg et al. ........................ | 128/754 |
| 5,375,608 | 12/1994 | Tiefenbrun et al. ..................... | 128/754 |
| 5,437,645 | 8/1995 | Urban et al. ............................. | 604/165 |
| 5,687,739 | 11/1997 | McPherson et al. ..................... | 128/754 |

FOREIGN PATENT DOCUMENTS 198770  10/1965  Sweden .

OTHER PUBLICATIONS

*Breast Ultrasound for Surgeons*, Edgar D. Staren, M.D. PhD. et al., The American Surgeon, pp. 108–112, Feb. 1996.
*Surgical Office–Based Ultrasound of the Breast*, Edgar D. Staren, M.D., PhD., The American Surgeon, pp. 619–627, Jul. 1995.

*Primary Examiner*—Cary O'Connor
*Assistant Examiner*—Charles Marmor, IV
*Attorney, Agent, or Firm*—Amin, Eschweiler & Turocy L.L.P.

[57] ABSTRACT

A guide assembly for performing a biopsy with a biopsy device having an elongated and substantially hollow cylindrical barrel is described. The guide assembly includes a bracket which is selectively movable relative to a base. The bracket has a longitudinal opening formed through a housing portion of the bracket into which the biopsy device may be mounted for guiding the biopsy device into desired tissue.

24 Claims, 6 Drawing Sheets

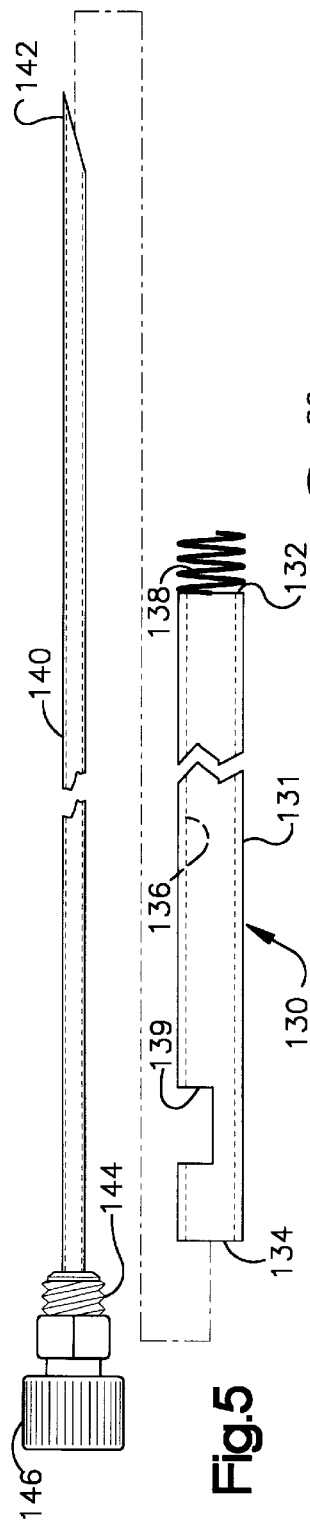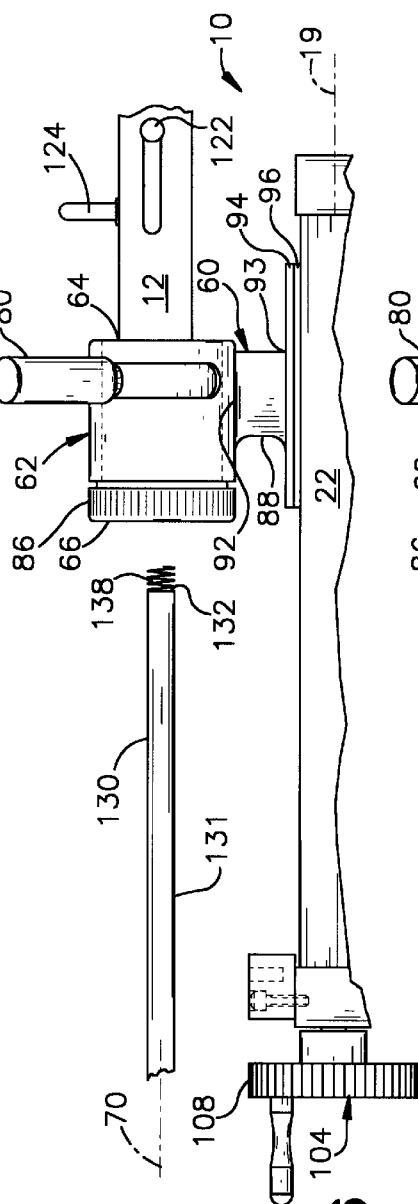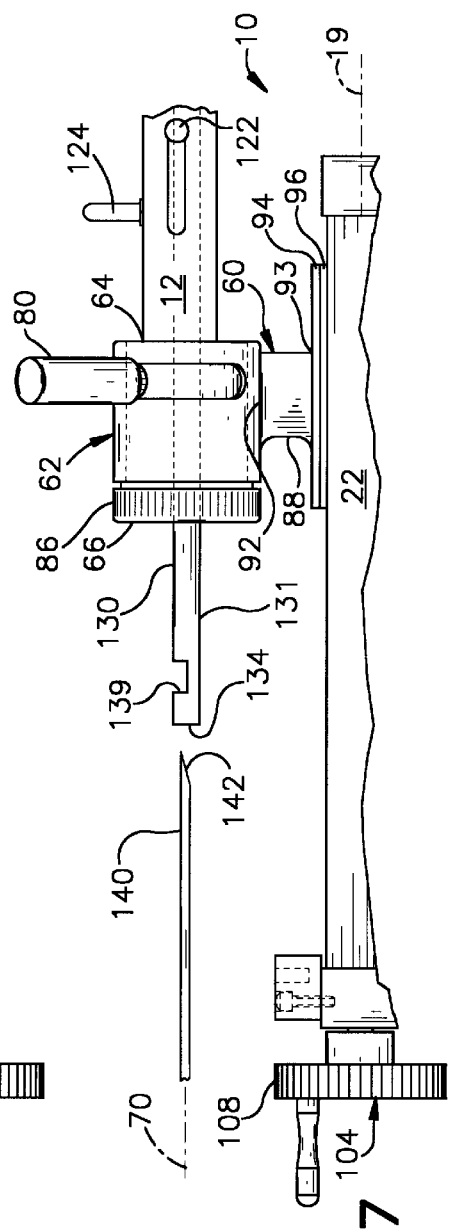

GUIDE ASSEMBLY FOR A BIOPSY DEVICE

RELATED APPLICATION

This application claims the benefit of U.S. Provisional Patent Application Ser. No. 60/061,882, which was filed Oct. 10, 1997.

TECHNICAL FIELD

The present invention relates generally to a guide assembly and, more particularly, to a guide assembly for guiding a biopsy device into preselected tissue of a patient.

BACKGROUND OF THE INVENTION

With an increasing occurrence of cancer, there is substantial research and development concerning biopsy devices and procedures for obtaining tissue samples from patients suspected of having lesions or other tissue abnormalities. One area of particular interest relates to the evaluation and analysis of nonpalpable breast abnormalities. In order to detect a lesion or abnormality in breast tissue, a typical first step is to diagnose the suspected area by conventional methods, such as mammography or ultrasound. In situations where the diagnosis is indeterminate, suspicious, or the lesion appears malignant, a core biopsy is routinely performed to evaluate the tissue.

Two common types of core biopsies that are being performed are stereotactic biopsies and ultrasound-guided core biopsies. Candidates for such core biopsies are typically selected based on the mammographic or sonographic appearance of the lesion. Core biopsies are, relatively speaking, less invasive and less costly than the open surgical biopsies, especially in situations where the lesion is found to be benign.

With conventional core biopsy equipment, more than one core biopsy or an open surgical biopsy often may be required. This may occur, for example, in a situation where technical difficulties during the biopsy procedure prevent an accurate biopsy or, alternatively, where there is a lack of correlation between the biopsy specimen and the radiographic findings. This is particularly prevalent where a conventional core biopsy extracts fatty tissue, missing the target tissue by mere millimeters.

SUMMARY OF THE INVENTION

The present invention is directed to a guide assembly which includes a base having a first end, a second end spaced apart from the first end, a first surface and a second surface. A longitudinal axis extends through the first and second ends of the base. A bracket includes a bracket housing having a first end, a second end and a generally cylindrical, longitudinal opening extending through the first and second ends of the bracket housing. The bracket opening has an axis extending through the bracket opening generally parallel to the base axis. The bracket is connected with the base for selectable movement of the bracket relative to the base between the first and second ends of the base. The bracket opening is configured for receiving a biopsy device therein.

Preferably, the guide assembly of the present invention is used in combination with a biopsy device which includes an elongated, hollow, and generally cylindrical barrel having an open first end and an open second end spaced apart from said first end. A longitudinal axis extends through the first and second ends of the barrel. A generally cylindrical cutter tip extends from said barrel first end coaxial with the axis of said barrel. The second end of said biopsy device may be removably positioned within said bracket opening such that the axis of said barrel is substantially coaxial with the axis of said bracket opening. Accordingly, one may effect selectable movement of said biopsy device generally parallel to the axis of said base upon movement of the bracket relative to the base and thus guide the cutter tip into preselected tissue to take a core biopsy.

BRIEF DESCRIPTION OF THE DRAWINGS

A preferred embodiment of the present invention is illustrated in the drawings in which:

FIG. 5 is a side view of a preferred embodiment of a retractor and needle;

FIG. 6 is a side view of part of the guide assembly and biopsy device of FIG. 4, illustrating part of a biopsy procedure;

FIG. 7 is a side view, similar to FIG. 6, illustrating another step of a biopsy procedure.

DESCRIPTION OF PREFERRED EMBODIMENTS

Figure 1:
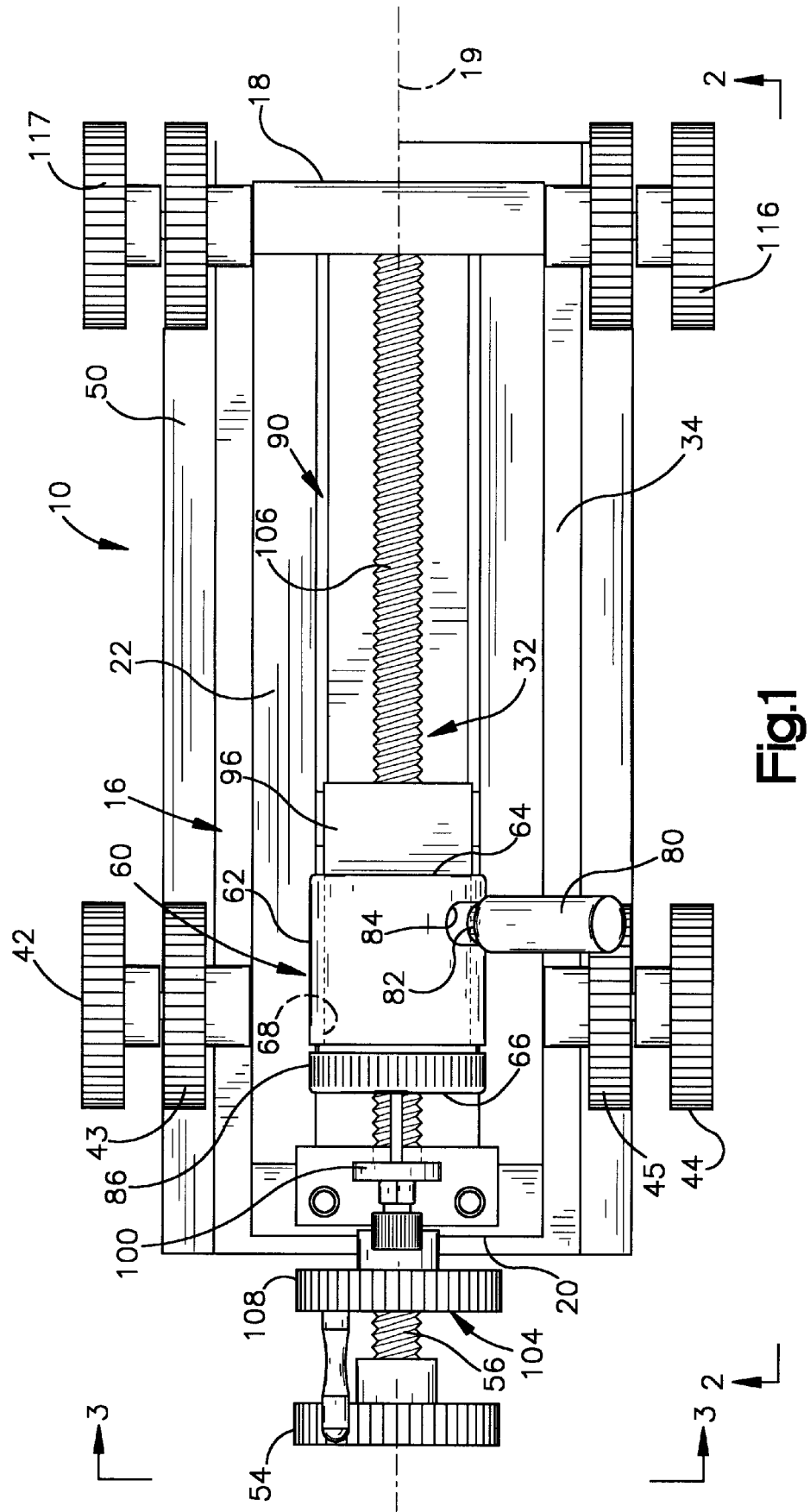
FIG. 1 is a top view of a guide assembly in accordance with a preferred embodiment of the present invention.
Figure 2:
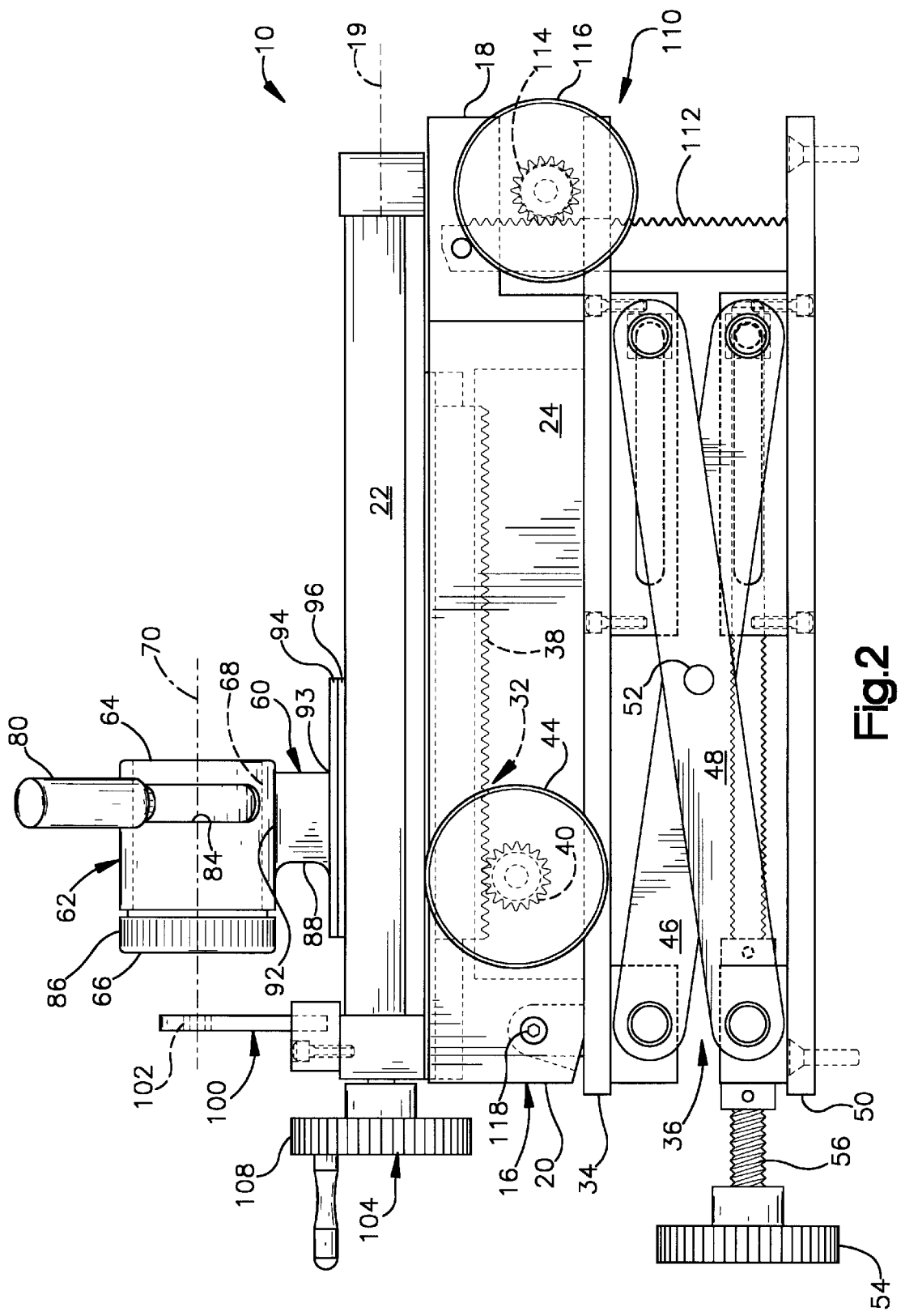
FIG. 2 is a side view of the apparatus of FIG. 1.
Figure 3:
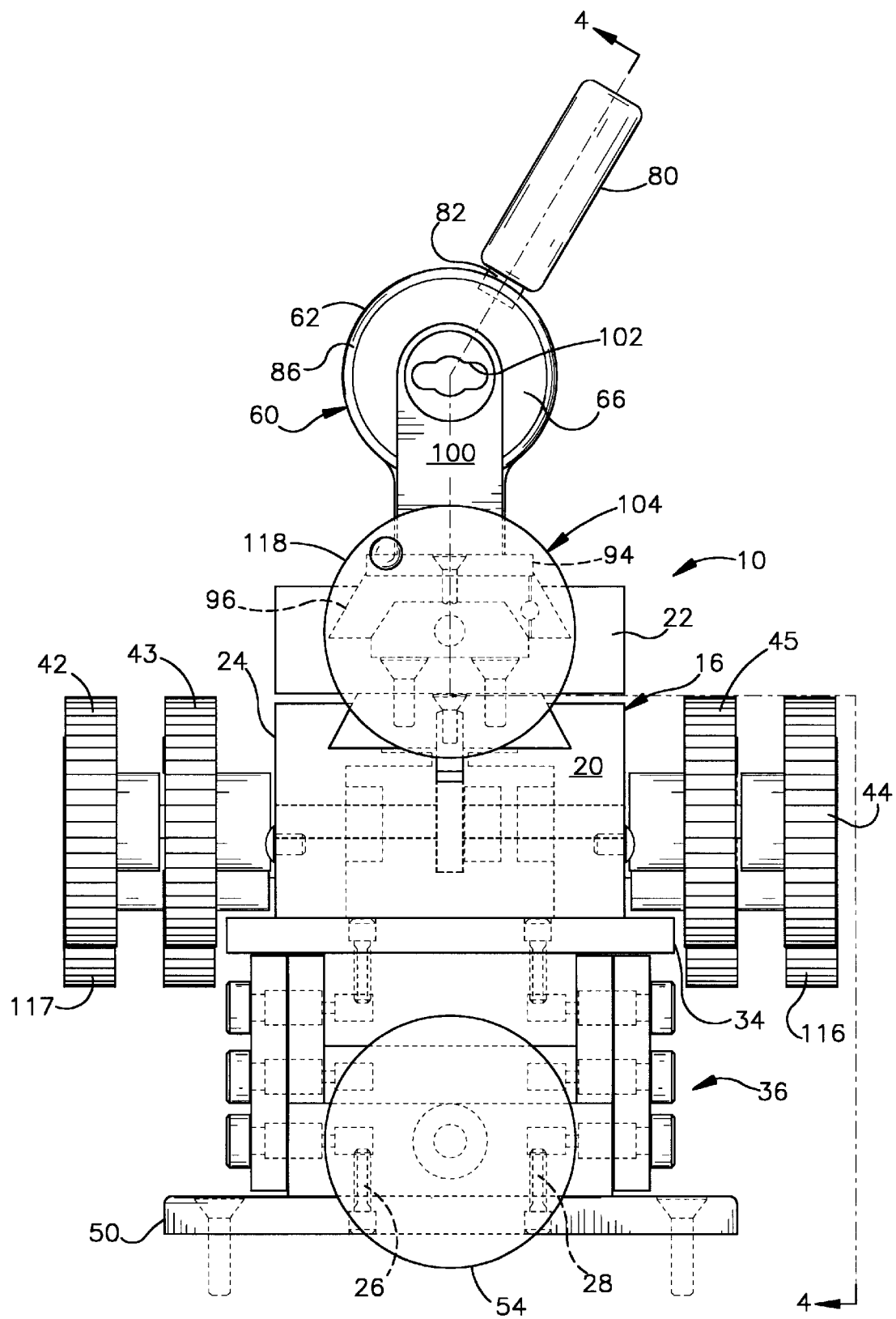
FIG. 3 is a front view of the apparatus of FIG. 1.

FIGS. 1–3 illustrate a preferred embodiment of a guide assembly, generally indicated as 10, in accordance with the present invention. The guide assembly 10 is primarily intended for guiding a biopsy device, indicated at 12 in FIGS. 4 and 6–8, into preselected tissue, such as to perform a core biopsy procedure.

Preferably, the biopsy device 12, such as shown in FIGS. 4 and 6–8, has an elongated and substantially hollow cylindrical barrel 14 extending from a rear open end portion 15. A preferred embodiment of a biopsy device 12 is shown and described in U.S. Pat. No. 5,687,739, which is assigned to Interventional Concepts, Inc. and which is incorporated herein by reference. It will be understood and appreciated by those skilled in the art that other biopsy devices also may be used in combination with the guide assembly 10 of the present invention.

Referring to FIGS. 1 through 3, the guide assembly 10 includes base 16 having a first end 18, a second end 20 spaced a predetermined distance apart from the first end 18. A longitudinal axis 19 extends through the first and second ends 18 and 20, respectively. The base 16 also includes a top potion 22 and a lower portion 24. Preferably, the base 16 may be mounted to a biopsy procedure table, such as to a Fischer Mammotest Table. The lower portion 24 of the base 16 also may be affixed to an upper part 34 of an optional vertical adjustment assembly 36. The vertical adjustment assembly 36 may then be attached to a suitable procedure table by threaded fasteners 26 and 28 or by any other conventional mounting device.

An elongated base guide mechanism 32 preferably is connected with the top portion 22 and lower portion 24 of the base 16, extending between its first and second ends 18 and 20, respectively. The base guide element 32 provides for movement of the top potion 22 relative to the lower portion 24 and the structure to which it may be mounted. Preferably, the guide mechanism 32 is configured to provide for movement of the top portion 22 of the base 16 substantially parallel to the axis 19.

In the preferred embodiment, the guide mechanism 32 is formed of a gear rack 38 having a plurality of teeth which meshingly engage an annular gear 40 to provide for the selectable movement of the top portion 22 of the base 16 relative to the lower portion 24. At least one and preferably two knobs 42 and 44 are connected with the gear 40 on opposite sides of the guide assembly 10. Rotation of either knob 42 or 44 is transferred to the gear to effect linear movement of the top portion 22 of the base 16 parallel to the axis 19. Each knob 42 and 44 preferably includes a corresponding locking mechanism, such as locking knobs 43 and 45, connected with the guide mechanism 32 coaxial with the knobs 42 and 44. The locking knobs 43 and 45 may be tightened to fix the top portion 22 relative to the lower portion 24.

It is to be understood and appreciated that other approaches may be used to provide for the selectable adjustment of the top portion 22 of the base 16. A spring-release latch or other conventional adjustable coupling known in the art, for example, may be used to selectively adjust the top portion 22 of the base 16 to a desired location.

The optional vertical adjustment assembly 36 advantageously provides for vertical adjustment of the base 16 to further facilitate positioning the biopsy device 12. Preferably, the upper plate 34 of the vertical adjustment assembly 36 is operatively connected with the lower portion 24 of the base 16. The upper plate 34 is connected with one end of at least two connecting arms 46 and 48 interconnected in the shape of an X. The arms 46 and 48 pivot relative to one another about a pivot hinge 52. Another end of each arm 46 and 48 is connected to a lower plate 50 of the vertical adjustment assembly 36. Upon urging ends of the arms 46 and 46 toward or away from each other, the distance between upper and lower mounting plate 34 and 50, respectively, may be adjusted. Preferably, a knob 54 is affixed to an elongated threaded rod 56 having one end connected with the end of arm 46 or 48 adjacent the lower plate 50. Rotation of the knob 54 provides for controlled movement of the arms 46 and 48, thereby raising or lowering the base 16 relative to the lower plate 50.

It will be understood and appreciated that other mechanisms may be used for raising and lower the base 16.

The guide assembly 10 also includes a bracket 60 having a bracket housing 62 which is spaced from the top portion 22 of the base 16. The bracket housing 62 includes a first end 64, a second end 66 and a longitudinal opening 68 formed completely through the first and second ends. Preferably, the diameter of the bracket opening is at least equal to the inner diameter of a biopsy device to be used so that various equipment may be passed through both the bracket opening and the biopsy device. The bracket opening 68 has an axis 70 extending longitudinally through the opening substantially parallel to the axis 19 of the base 16.

Figure 4:
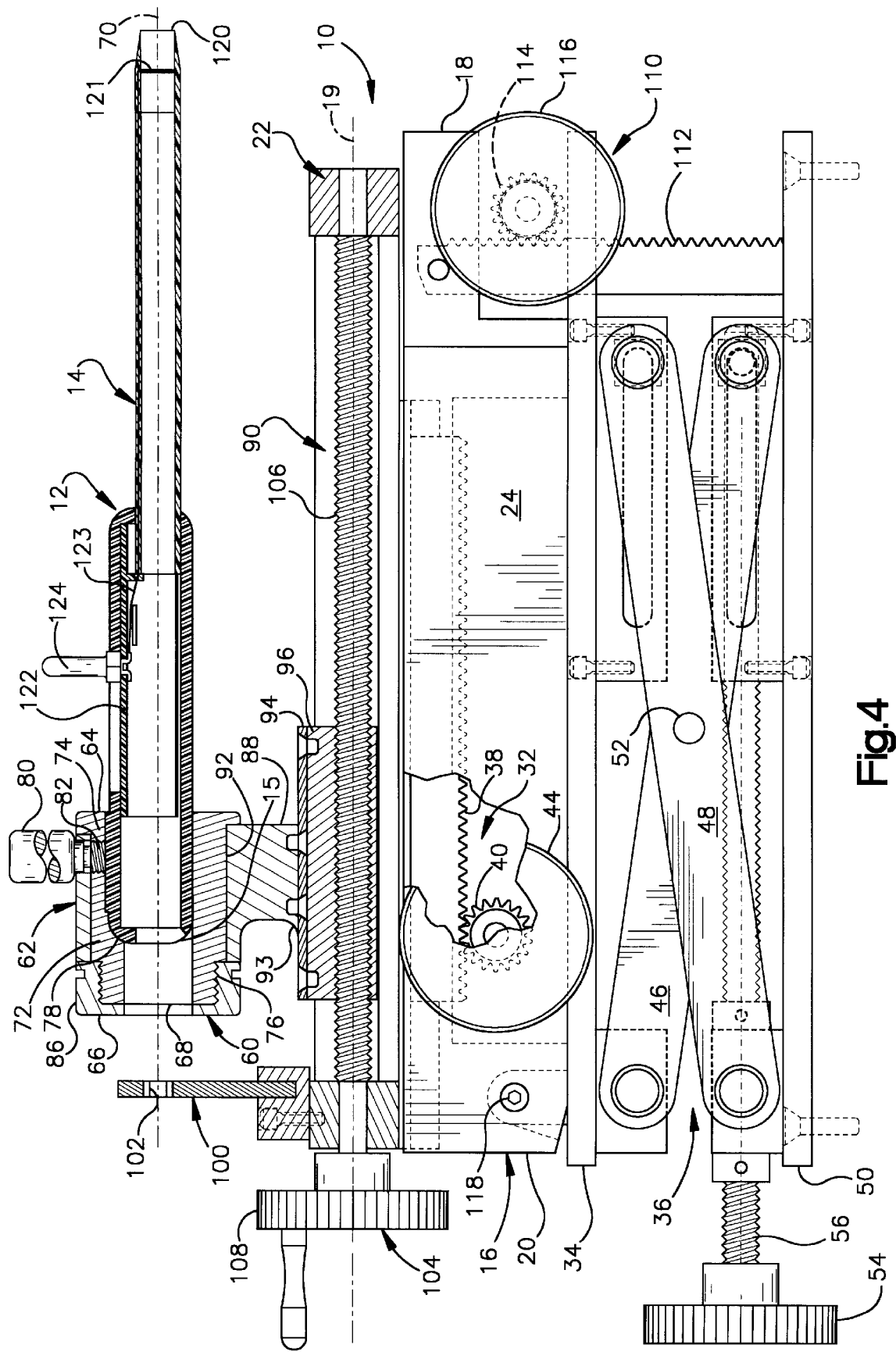
FIG. 4 is a side view of the apparatus of FIG. 1, partially in section taken along line 4—4 of FIG. 3, illustrating its use with a biopsy device in accordance with a preferred embodiment of the present invention.

As shown in FIG. 4, a receptacle 72 preferably is positioned within the bracket housing 62 adjacent the first end 64, preferably coaxial with the bracket opening 68. The receptacle 72 is configured for receiving a biopsy device, such as the biopsy device 12.

The receptacle 72 preferably is formed of cylindrical chamber dimensioned and configured according to the dimensions and configurations of the rear end 15 of the biopsy device 12 which is to be inserted therein. The receptacle 72 has a first end 74, or opening, positioned adjacent to the first end 64 of the bracket housing 62. The receptacle 72 terminates in a second end 76 positioned between the first and second ends 64 and 66 of the bracket housing 62. The second end 76 of the receptacle 72 may include a retaining element 78, suitably in the form of a radially extending ledge, for limiting the amount which a biopsy device 12 may be inserted within receptacle 72. Preferably, the receptacle 72 is mounted for rotation within the bracket housing 62, such that receptacle 72 may conveniently be rotated about the axis 70 of the bracket opening 68.

In order to releasably fix a biopsy device within receptacle 72, a threaded rod 82 extends from a handle 80 and is threaded into a corresponding bore of the side wall of the receptacle 72. Accordingly, the threaded rod 82 may be threaded against the biopsy device 12 to maintain it at a fixed position within receptacle 72. Preferably, the threaded rod 82 of the handle 80 extends through an elongated circumferential slot 84 formed in the bracket housing 62. The slot 84 limits the amount of angular rotation of the receptacle 72 through the contact of the threaded rod 82 of the handle 80 and ends of the slot.

An annular knob 86 also is located at the second end 66 of the bracket housing 62 to rotate the receptacle 72 about the axis 70 of the bracket opening 68. The knob 86 preferably includes axially extending ridges located circumferentially about the knob. The ridges ensure a positive grip can be made for the desired rotation of the receptacle 72. The knob 86 also has a central opening which provides access into the receptacle 72 and through the housing 62.

The bracket 60 also includes an arm 88 which engages an elongated bracket guide 90 which is located adjacent the top portion 22 of the base 16. The arm 88, which may be part of or separate from the bracket 60, has a first end 92 attached to the lower side of the bracket housing 62. A second end 93 of the arm 88 is spaced apart from its first end 92 and attached to a plate 94. The plate 94 is dimensioned and configured for mating engagement with the bracket guide 90.

The bracket guide 90 extends generally parallel to the axis 19 between the first and second ends 18 and 20, respectively, of the base 16. Preferably, the bracket guide 90 includes an elongated trapezoidal channel formed in the top portion 22 of the base 16 extending longitudinally between the ends 18 and 20 of the base. The plate 94 is attached to a guide element 96, such as shown in the sectional view of FIG. 4, to provide for selective positioning of the bracket 60 along the channel of the bracket guide 90.

In order to provide for controlled movement of the bracket 60 relative to the top portion 22 of the base 10, the guide assembly 10 preferably includes an advancement assembly, indicated at 104. The advancement assembly 104 is mounted within the top portion 22 of the base 16 to provide for adjustable lateral movement of the bracket 60 relative to the top portion 22 of the base 16. Preferably, the advancement assembly 104 includes an elongated threaded rod 106 which extends the length of the bracket guide 90 substantially parallel to the axis 19. The guide element 96 has a threaded bore formed longitudinally through the guide element 96 into which the rod 106 is threaded. Rotation of the rod 106 about its axis effects axial movement of the guide element 96 along the bracket guide 90. This, in turn, provides for movement of the attached bracket 60, such that the bracket opening 68 moves parallel to axis 19 of the base 16. An appropriately dimensioned knob 108 is connected to the threaded rod 106. The knob 108 preferably is dimensioned to have a preselected turn ratio so as to provide for a predefined lateral movement of the bracket 60 for each 360° of angular rotation of the knob 108. Accordingly, when a biopsy device is received within the receptacle 72, such as the device 12 shown in FIGS. 4 and 7, the biopsy device may be guided into preselected tissue more precisely.

In order to assist with the alignment and positioning of the biopsy device 12, the guide assembly 10 also includes a needle guide 100, which extends outwardly a predetermined distance from the top portion 22 of the base 16 adjacent the second end 20. Preferably, the needle guide 100 is removably attached to the base to facilitate the insertion of surgical equipment through the bracket housing 62. The needle guide 100 has an aperture 102, formed therethrough substantially coaxial with bracket opening axis 70. The aperture 102 preferably is threaded.

A tilt mechanism 110 also may be provided to adjust the tilt angle of the first end 18 of the base 16 relative to the lower plate 50 of the vertical adjustment assembly 36. Preferably, the tilt mechanism 110 is substantially similar to the lateral guide mechanism 32. The tilt mechanism 110 includes a rack 112 with teeth extending vertically between the first end 18 of the base 16 and the plate 50. A gear 114 meshingly engages the rack 112 to move the first end 18 of the base 16 relative to the lower plate 50. Two knobs 116 and 117 are coaxially connected with the gear 114 to facilitate the angular adjustment of the assembly 10. A pivot hinge 118 pivotally connects the second end 20 of the base 16 with the top plate 34 of the vertical adjustment assembly 36. The pivot hinge 118 permits angular adjustment of the base 16, preferably to at least 15° relative to the lower plate 50.

FIGS. 4 and 7 illustrate a preferred embodiment of the biopsy device 12. The device 12 is similar to that disclosed in the previously incorporated U.S. Pat. No. 5,687,739.

In general, the biopsy device 12 includes an elongated cylindrical barrel 14 having a cutter tip 120 at one end, which is preferably a sharpened circular cylindrical tip. The rear end 15 is open to permit the insertion of additional equipment and devices into and through the generally hollow biopsy device. Such additional equipment, for example, may be used for contacting or viewing preselected tissue proximal to cutter tip 120. The preferred biopsy device 12 also includes a cutting element, such as a loop of wire 121, located adjacent to the cutter tip 120 for making a cut transverse to the axis of the cutter barrel 14. Other types of cutting elements also may be used.

The biopsy device 12 includes a trigger 122 operatively connected to the cutting element 121, suitably by a length of wire 123. The connecting wire 123 may also be used to form the loop 121 which operates as the cutting element positioned within barrel 14 adjacent to cutter tip 120. Movement of the trigger 122 toward the rear end 15 effects the cutting by the cutting element 121, preferably transverse to the axis 70.

Figure 8:
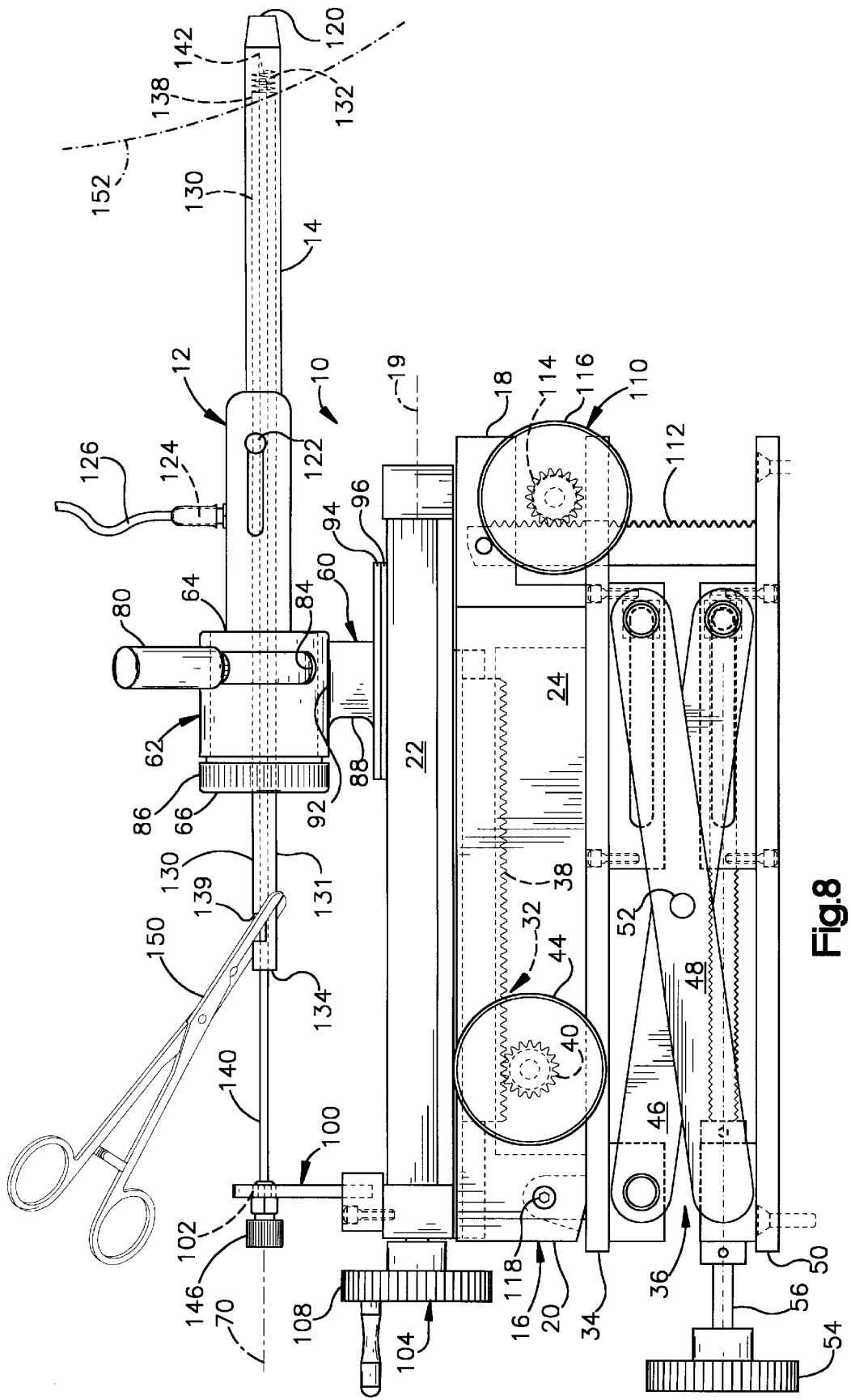
FIG. 8 is a side view of the guide assembly and biopsy device of FIG. 4, illustrating yet a another step of a biopsy procedure in accordance with a preferred embodiment of the present invention.

Preferably, the cutting element 121 is electrically coupled to an electrically conductive finger 124 extending from biopsy device 12 through the wire 123. The finger 124 may be attached to a power source via a conventional electrosurgery cable 126, as shown in FIG. 8. The cable 126 may be used to apply a desired amount of power to facilitate severing a desired tissue sample from the host tissue. In general, approximately 25 watts of power for about 3 to about 5 seconds should be sufficient.

Referring to FIGS. 4–7, the tissue from which the desired sample is to be taken may conveniently be located by either mammography or ultrasound. After securing the biopsy device 12 within receptacle 72, an elongated needle guide or retractor 130 is inserted through the open rear end 15 of biopsy device and positioned within device.

As illustrated in FIG. 5, the retractor 130 includes an elongated, cylindrical, and hollow body portion 131 having a first end 132 and a second end 134 spaced apart from the first end. A longitudinal aperture 136 is formed completely through the retractor body portion 131. The retractor body portion 131 may be formed of a generally rigid material, such as a thermoplastic, thermosetting, metal or other suitable material. While the cylindrical body portion preferably is formed of a right, circular cylinder, it will be understood and appreciated that other cylindrical shapes, e.g. rectangular or polygonal, also could be used.

A cylindrical, helical member 138 extends from the first end 132 of the retractor body portion 131 coaxial and coextensive with the cylindrical sidewall of the body portion of the retractor 130. Preferably, the helical member 138 is formed of at least one turn of a substantially rigid, helical coil, similar to a conventional cork-screw. The helical member 138 may be formed of a material different from the elongated body portion 131 of the retractor 130 or, alternatively, it may be formed as part of the retractor. The helical member 138 may be formed of a metal or any other suitable rigid material. Advantageously, the inner and outer diameters of helical member 138 are substantially equal to the respective inner and outer diameters of the body portion 131 of the retractor 130, such that the aperture 136 also extends completely through the helical member 138.

The retractor 130 also includes a slot 139 formed in the sidewall of the retractor adjacent its second end 134. The slot 139 provides access to the aperture 136 so that an article, such as the elongated locator needle 140, may be gripped and held at a fixed position relative to the retractor 130.

The elongated locator needle 140 is used to locate the target tissue specimen, suitably with the assistance of ultrasound or mammography. The needle 140 has a pointed and sharpened first end 142 to facilitate movement through tissue. The needle also includes a second end 144 attached to a knob 146 having a threaded fastener. The threaded fastener of knob 140 is configured for threading into the corresponding threaded bore 102 of the needle guide 100. This enables the locator needle 140 to be fixed relative to the base 16, such as after being positioned adjacent to the target tissue specimen, while the bracket housing 62 and the biopsy device 12 may be advanced along the base. The needle may be a solid rod or hollow.

The needle 140 may be inserted through the aperture 136 and helical member 138 of the retractor 130. The aperture 136 of the retractor body portion 131 and the helical member 138 thus are preferably dimensioned and configured for guiding the needle 140 coaxially through the retractor 130 and its helical member.

It will be appreciated by those skilled in the art that the retractor 130 preferably is longer than the biopsy device 12 and that the locator needle 140 preferably is longer than the retractor.

With preferred embodiments of the structure of the guide assembly 10 and the biopsy device 12 described above, it will be apparent to those skilled in the art that the guide assembly provides an effective tool for guiding the biopsy device into preselected tissue. The biopsy device 12 is mounted within the receptacle 72 by tightening locking handle 80. Next, as shown in FIG. 6, the retractor 130 is inserted through the bracket knob 86, into the bracket opening 68 within the housing 62 and a predetermined distance into the barrel 14 of the biopsy device 12.

Referring to FIG. 7, the locator needle 140 is then inserted coaxially through the aperture 136 of the retractor 130 substantially coaxially with the axis 70 of the bracket opening 68. The needle guide 100 is secured to base 16, preferably after the insertion of the needle within the retractor 130.

Based upon the radiograph or sonograph, the assembly 10 is adjusted, such that the axis 70 of bracket opening 68 is aligned with the tissue sample. For example, the vertical, angular and lateral positioning of the base 16 may be adjusted, such as described above. A small incision is made in the patient's skin, indicated as phantom line 152 in FIG. 7, through which the cutter tip 120 of the biopsy device is inserted. The area of the skin 152 through which the biopsy device 12 is to be inserted through should be opened sufficiently wide, such that cutter tip 120 does not contact the skin when inserted therethrough. The first end 142 of the needle 140 is manually advanced along the axis 70 until it is appropriately positioned within the patient adjacent the desired tissue sample. The needle 140 may then be fixed to desired position within the needle guide 100.

The cylindrical helical member 138 of the retractor 130 advantageously is configured to retract and hold desired tissue. This is accomplished by axially advancing the retractor 130 along the needle 140 until the target tissue specimen is at its first end 138. This conveniently may be confirmed via sonography or ultrasound or by observing indicia located along the length of the needle 140. The retractor 130 is then rotated about the axis 70, preferably about one full turn (360°) into the tissue. Over rotation may result in breaking loose part of the tissue sample. It will be appreciated that attachment with the target tissue sample is facilitated by the cylindrical shape of the helical member 138.

A hemostat 150 or other suitable gripping device is placed in the slot 139 located at the rear of the needle guide 92 to secure the retractor 130 to the fixed needle 140. The hemostat 150 holds the retractor 130 and attached tissue in place as the biopsy device 12 is moved. With the needle guide 100 fixed, the bracket 60 and the biopsy device 12 are then advanced forward along bracket guide 90 relative to the base 16, such as by the advancement assembly 104.

In order to facilitate the cutting action of cutter tip 120, knob 86 may be repeatedly rotated in opposite directions about the axis 70 as the biopsy device 12 is urged into the target tissue. This creates a slicing action with cutter tip 120. In general, such rotation will substantially reduce the pressure required to cut the target tissue sample. The cutter tip 120 should be advanced beyond the first end 142 of the needle assembly 140 and the first end 132 of the retractor 130 so that a sufficient specimen will remain in the barrel 14 upon being cut. The amount of insertion may conveniently be designated by an indicia on the needle assembly or the base 16 and/or confirmed radiographically sonographically or by ultrasound.

In order to facilitate and promote coagulation, the electrosurgery cable 126 may be attached to the finger 124 and an appropriate amount of electrical power, suitably about 25 watts, may be applied for a predetermined time period, such as about 3 to about 5 seconds. Next, the trigger 122 of the biopsy device 12 may be pulled to effect movement of the cutting element transverse to the axis 70. This results in severing the tissue sample from the host tissue, such that the tissue sample remains within barrel 14 connected with the helical member 138 of the retractor 130.

The needle 140 may be pulled carefully back and removed from assembly 10. At this stage, needle guide 100 should also be removed. The desired tissue sample is attached to the helical member 138 of the retractor 130. The retractor 130 and tissue sample simply may be removed from the biopsy device 12 and guide assembly 10. However, it is possible that the sample may remain within the elongated barrel 14 of the biopsy device 12. If this occurs, a conventional pair of double-jaw forceps may be used to explore the barrel 14 for the sample. A fiber-optic viewing device may be used to facilitate searching for and removing the tissue sample.

With the biopsy device positioned within the preselected soft tissue of the patient, the combination of the biopsy device and guide assembly 10 advantageously form an operable trocar. The cutter tip 120, which defines the front end of the trocar, is positioned at a preselected position in the patient, generally adjacent to suspect tissue. Accordingly, the bracket opening 68 and the hollow biopsy device 12 provide a passage to such tissue. Advantageously, additional procedures may be performed through the trocar, such as where the biopsy specimen may be inadequate.

The inner diameter of cylindrical barrel 14 determines the diameter of the trocar device and, thus, establishes the size of instruments that may be inserted therethrough. For example, a cylindrical barrel 14 having a diameter of about 7 mm enables the use of conventional 5 mm forceps. In addition, a fiber-optic viewing device, such that images can be viewed through an eye piece or be displayed on a monitor, also may be inserted through the bracket opening 68, through the biopsy device 12 and into the soft tissue for further exploration and analysis.

An additional advantage of the trocar device formed by the assembly 10 of the present invention in combination with the biopsy device 12 is that in situations where the tissue sample is inadequate, conventional surgical instruments may be inserted through the trocar device for excising additional tissue samples from the suspected area, without having to remove the biopsy device and commence an additional biopsy procedure. In addition, coagulation and suction devices may also be inserted through the trocar and contact the area from which the tissue sample was taken to control bleeding more effectively.

Numerous variations and modifications of the present invention, all within the scope of this invention, will readily occur to those skilled in the art. All such modifications and variations are considered to be fully be covered by the appended claims.

Having described the invention, the following is claimed:

1. A guide assembly comprising:

a base having a first end, a second end spaced apart from said first end, a first surface, a second surface, and a longitudinal axis extending through said first and second ends of said base, said base having a guide portion formed in said base extending between said first and second ends of said base parallel with the axis of said base;

a bracket which includes a bracket housing having a first end, a second end and a generally cylindrical, bore extending through the first and second ends of said bracket housing, said bore having a longitudinal axis extending through said bore generally parallel to the axis of said base, said bracket being connected with the said base for selectable movement of said bracket relative to said base between the first and second ends of said base, said bracket housing having a receptacle positioned within and generally coaxial with said bore adjacent the first end of said bracket, said receptacle being configured for receiving a biopsy device within said receptacle, whereby a portion of the biopsy device may be received within the receptacle substantially parallel with the axis of the bore and guided into preselected tissue upon movement of the bracket relative to the base.

2. A guide assembly as set forth in claim 1 wherein said base further includes means for moving said bracket relative to said base such that, when moved, said receptacle moves substantially parallel with the axis of said base and substantially coaxially with the axis of said bore.

3. A guide assembly as set forth in claim 1 further including an elongated channel formed in the first surface of said base and extending longitudinally between the first and second ends of said base substantially parallel to the axis of said base, part of said bracket mounted for movement within said elongated channel.

4. A guide assembly as set forth in claim 3, wherein said bracket further includes a connecting arm having spaced apart first and second ends, the first end of said arm attached with said bracket housing and the second end of said arm connected within said elongated channel of said base to provide for selectable movement of said bracket substantially parallel to the axis of said base.

5. A guide assembly as set forth in claim 1 wherein said receptacle includes a generally cylindrical chamber positioned within and substantially coaxial with said bore, said cylindrical chamber having an open first end spaced apart from an open second end adjacent the second end of said bore.

6. A guide assembly as set forth in claim 5, wherein said cylindrical chamber further includes a radially extending retaining element located adjacent the open second end of said cylindrical chamber for limiting the amount which a biopsy device may be inserted within said receptacle.

7. A guide assembly as set forth in claim 1 wherein said receptacle includes defines a generally cylindrical chamber positioned within and substantially coaxial with said bore, said cylindrical chamber having an open first end spaced apart from an open second end, said receptacle being rotatable relative to said bracket about the axis of said bore, whereby upon rotation of the receptacle about the bore axis, a biopsy device positioned within the receptacle also is rotated about the bore axis.

8. A guide assembly as set forth in claim 1 further comprising a locking mechanism attached to said base for releasably fixing said bracket at a desired location between the first and second ends of said base.

9. A guide assembly as set forth in claim 1 further comprising a needle guide support attached to and extending outwardly from the first surface of said base adjacent the second end of said base, said needle guide support having an aperture formed through said needle guide support at a location substantially coaxial with said bore axis.

10. A guide assembly as set forth in claim 1 in combination with a biopsy device, said combination comprising:
said biopsy device including:
an elongated, hollow, and generally cylindrical barrel having an open first end, an open second end spaced apart from said first end and a longitudinal axis extending through said barrel first and second ends; and
a generally cylindrical cutter tip extending from said barrel first end coaxial with the axis of said barrel, the second end of said biopsy device being removably positioned within said receptacle such that the axis of said barrel is substantially coaxial with the axis of said bore for effecting selectable movement of said biopsy device generally parallel to the axis of said base, whereby the combination is operative to form a trocar apparatus.

11. A combination as set forth in claim 10, further including an elongated retractor having spaced apart first and second ends and an axis extending through the first and second ends of said retractor, said retractor having a cylindrical, helical portion located at the first end of said retractor substantially coaxial with the axis of retractor, said retractor being dimensioned and configured for axial movement within said hollow barrel of said biopsy device and through said cutter tip.

12. A combination as set forth in claim 11, wherein said retractor further includes a hollow cylindrical sidewall extending between the first and second ends thereof, said helical portion having a cylindrical sidewall portion substantially coextensive with said sidewall of the retractor, an aperture being formed through the first and second ends of said retractor for coaxial movement of an elongated locator needle through said retractor, whereby the locator needle may be inserted coaxially through the aperture of the retractor and extend beyond the helical portion of the retractor.

13. A combination as set forth in claim 12, wherein said retractor has a notch formed in said cylindrical sidewall of said retractor adjacent the second end of said retractor to provide an opening to the interior of said retractor for inhibiting movement of the locator needle relative to said retractor.

14. A guide assembly comprising:
a base having a first end, a second end spaced a predetermined distance apart from said first end, a first surface and a second surface, said base also having an axis extending through the first and second ends of said base;
an elongated base guide element positioned adjacent to the second surface of said base and extending between the first and second ends of said base, said base guide element including means for effecting movement of said base substantially parallel to the axis of said base;
a bracket having a generally cylindrical housing, said housing having a first end, a second end, and a bore extending through said bracket housing first and second ends, said bore having a longitudinal axis extending through said bracket housing first and second ends generally parallel to the axis of said base; and
means operatively connected with said bracket and said base for effecting selectable movement of said bracket relative to said base between said base first and second ends, such that the axis of said bore moves in a direction substantially parallel to the axis of said base.

15. A biopsy apparatus comprising:
an elongated cylindrical member having first and second spaced apart ends and a longitudinal aperture extending through said first and second ends, said cylindrical member having an axis extending through the first and second ends thereof;
a cutter tip located at said first end of said cylindrical member substantially coaxial with the aperture of said cylindrical member;
a cutting element located within said cylindrical member adjacent said cutter tip for effecting a cut within said cylindrical member substantially transverse to the axis of said cylindrical member; and an elongated retractor having first and second ends and an axis extending through the first and second ends of said retractor, said retractor having a hollow and substantially cylindrical sidewall portion extending between the first and second ends of said retractor, said retractor having a substantially cylindrical, helical portion located at the first end of said retractor, said helical portion being substantially coaxial with the axis of said retractor, said retractor being configured for axial movement within the aperture of said cylindrical member to a location beyond said cutter tip.

16. A biopsy apparatus as set forth in claim 15 wherein said retractor has an aperture extending through the first and second ends of said sidewall portion of said retractor for coaxial movement of a locator needle through the aperture of said retractor, said cylindrical helical portion having a cylindrical sidewall portion which is substantially coextensive with said sidewall portion of the retractor to permit movement of the locator needle through the retractor and to a location beyond said helical portion.

17. A biopsy apparatus as set forth in claim 16, wherein said retractor has a notch formed in the cylindrical sidewall portion of said retractor adjacent the second end of said retractor to provide an opening to the interior of said retractor, whereby an object located within the aperture of the retractor may be accessed.

18. A biopsy apparatus as set forth in claim 15, wherein said cylindrical helical portion is affixed at the first end of said retractor substantially coaxially with the axis of said retractor.

19. A biopsy apparatus as set forth in claim 18, wherein said retractor is formed of a plastic material.

20. A biopsy apparatus as set forth in claim 19, wherein said helical portion is formed of a metal material.

21. A biopsy apparatus as set forth in claim 15 in combination with a guide assembly to form a system for performing a biopsy, said system comprising:
a guide assembly including:
a base having a first surface, an opposing second surface, a first end, a second end spaced apart from said first end, and a longitudinal axis extending through said first and second ends of said base, a guide portion formed in the first surface of said base extending between said first and second ends of said base;
a bracket including a bracket housing having a first end, a second end and a generally cylindrical bore extending through the first and second ends of said bracket housing, said bore having an axis extending through said bore generally parallel to the axis of said base, said bracket housing being connected with the guide portion of said base for selectable movement of said bracket relative to said base between the first and second ends of said base, a portion of said biopsy device adjacent said second end being removably mounted within said bore with the axis of said cylindrical member of said biopsy device being substantially coaxial with the axis of said bore, whereby, upon movement of the bracket relative to the base, the cutter tip of the biopsy device is moved substantially parallel to the axis of the base.

22. A retractor apparatus for removing a biopsy specimen, said retractor comprising:
an elongated, cylindrical sidewall portion having a first end, a second end and an axis extending longitudinally through the first and second ends thereof a slot being formed in said cylindrical sidewall portion adjacent the second end of said cylindrical sidewall portion to provide access into an interior of said cylindrical sidewall portion; and
a cylindrical, helical member extending coaxially from the first end of the cylindrical sidewall portion, said helical member having at least one turn, whereby upon the helical member engaging the biopsy specimen and upon rotation of the retractor apparatus about the axis, the biopsy specimen attaches to the helical member of the retractor.

23. A retractor apparatus as set forth in claim 22, wherein said cylindrical sidewall portion and said helical member have substantially coextensive and coaxial sidewall portions through which an elongated aperture extends.

24. A retractor apparatus as set forth in claim 22, in combination with a biopsy device which is mountable within a guide assembly, said combination comprising:
said biopsy device including
an elongated cylindrical member having first and second spaced apart ends and a longitudinal aperture formed through said first and second ends, said cylindrical member having an axis extending through the first and second ends thereof,
a cutter tip located at said first end of said cylindrical member of said biopsy device substantially coaxial with the aperture of said cylindrical member of said biopsy device, and
a cutting element located within said cylindrical member of said biopsy device adjacent said cutter tip for effecting a cut within said cylindrical member of said biopsy device substantially transverse to the axis of said cylindrical member of said biopsy device,
said retractor being positioned within the aperture of said cylindrical member of said biopsy device and configured for axial movement within the aperture of said cylindrical member of said biopsy device,
said guide assembly including
a base having a first surface, an opposing second surface, a first end, a second end spaced apart from said first end, and a longitudinal axis extending through the first and second ends of said base, a guide portion located at the first surface of said base extending between the first and second ends of said base, and
a bracket including a bracket housing having a first end, a second end and a generally cylindrical bore extending through the first and second ends of said bracket housing, said bore having an axis extending through said bore generally parallel to the axis of said base, said bracket housing being connected with the guide portion of said base for selectable movement of said bracket relative to said base between the first and second ends of said base,
a portion of said biopsy device adjacent said second end being removably mounted within said bore with the axis of said cylindrical member of said biopsy device being substantially coaxial with the axis of said bore, whereby, upon movement of the bracket relative to the base, the cylindrical member of the biopsy device is moved substantially parallel to the axis of the base.

* * * * *